(12) United States Patent
Fortin et al.

(10) Patent No.: US 7,776,071 B2
(45) Date of Patent: Aug. 17, 2010

(54) FLEXIBLE VERTEBRAL LINKING DEVICE

(75) Inventors: Frédéric Fortin, Pessac (FR); Johann Robin, Mérignac (FR)

(73) Assignee: Paradigm Spine, LLC, New York, NY (US)

( * ) Notice: Subject to any disclaimer, the term of this patent is extended or adjusted under 35 U.S.C. 154(b) by 904 days.

(21) Appl. No.: 10/505,469

(22) PCT Filed: Jul. 17, 2002

(86) PCT No.: PCT/FR02/02547

§ 371 (c)(1),
(2), (4) Date: Aug. 20, 2004

(87) PCT Pub. No.: WO03/007828

PCT Pub. Date: Jan. 30, 2003

(65) Prior Publication Data

US 2005/0165396 A1   Jul. 28, 2005

(51) Int. Cl.
*A61B 17/70* (2006.01)
(52) U.S. Cl. .................................. 606/257
(58) Field of Classification Search ............ 606/61
See application file for complete search history.

(56) References Cited

U.S. PATENT DOCUMENTS

| | | | |
|---|---|---|---|
| 3,900,025 A | 8/1975 | Barnes | |
| 4,386,603 A | 6/1983 | Mayfield | |
| 4,445,674 A | 5/1984 | Clayton, Jr. | |
| 4,611,582 A | 9/1986 | Duff | |
| 4,658,809 A | 4/1987 | Ulrich et al. | |
| 4,747,394 A | 5/1988 | Watanabe | |
| 4,931,055 A | 6/1990 | Bumpus et al. | |
| 5,129,903 A | 7/1992 | Luhr et al. | |
| 5,130,356 A | 7/1992 | Feuerherd et al. | |
| 5,375,823 A | * 12/1994 | Navas | 623/17.15 |
| 5,395,370 A | 3/1995 | Müller et al. | |
| 5,503,413 A | * 4/1996 | Belogour | 280/11.225 |

(Continued)

FOREIGN PATENT DOCUMENTS

CA     2 451 977     11/1993

(Continued)

OTHER PUBLICATIONS

Office Action dated Jul. 17, 2006, in U.S. Appl. No. 10/760,075, filed Jan. 18, 2004.

(Continued)

*Primary Examiner*—Thomas C Barrett
*Assistant Examiner*—Nicholas Woodall
(74) *Attorney, Agent, or Firm*—Monument IP Law Group

(57) ABSTRACT

A flexible intervertebral linking device (1) is provided. The device (1) utilizes two sets of structures. A first structure (11) is a rigid structure (110, 112, 114, 116) preferably made of biocompatible metallic materials providing the device with good mechanical resistance by integral load transmission without deformation. A second structure (12) is a flexible or damping structure (121 and 122) made of biocompatible viscoelastic materials, permitting repeated elastic deformations. The combination of the two structures providing the device with both resistance and mechanical dampening of forces to which it is subjected, with the purpose of compensating for any deficiency in the flexibility of certain anatomical links of the human body.

15 Claims, 6 Drawing Sheets

U.S. PATENT DOCUMENTS

| | | |
|---|---|---|
| 5,672,175 A | 9/1997 | Martin |
| 5,700,263 A | 12/1997 | Schendel |
| 5,885,283 A | 3/1999 | Gittleman |
| 6,241,730 B1 | 6/2001 | Alby |
| 6,382,602 B1 | 5/2002 | Morrow |
| 6,402,750 B1 | 6/2002 | Atkinson et al. |
| 7,029,472 B1 | 4/2006 | Fortin |
| 2002/0151978 A1 | 10/2002 | Zacouto et al. |
| 2004/0097938 A1 | 5/2004 | Alleyne |
| 2004/0153067 A1 | 8/2004 | Smith et al. |
| 2005/0056979 A1* | 3/2005 | Studer et al. .......... 267/118 |
| 2005/0182401 A1 | 8/2005 | Timm et al. |
| 2005/0261685 A1 | 11/2005 | Fortin et al. |
| 2007/0149909 A1 | 6/2007 | Fortin et al. |

FOREIGN PATENT DOCUMENTS

| | | |
|---|---|---|
| DE | 2437752 A1 | 2/1976 |
| DE | 195 00 202 A1 | 7/1996 |
| EP | 0 576 379 A | 12/1993 |
| FR | 2692952 A1 | 12/1993 |
| FR | 2 717 370 A | 9/1995 |
| FR | 2 730 156 A | 8/1996 |
| FR | 2 774 581 A | 8/1999 |
| FR | 2814936 | 4/2002 |
| WO | WO 90/12553 A1 | 11/1990 |
| WO | WO 98/22033 | 5/1998 |

OTHER PUBLICATIONS

Office Action dated Apr. 18, 2008, in U.S. Appl. No. 10/760,075, filed Jan. 18, 2004.

Office Action dated Dec. 22, 2008, in U.S. Appl. No. 10/524,174, filed Mar. 3, 2006.

French Search Report and Written Opinion in Application No. FR 0510207, dated Jul. 25, 2006.

French Search Report in Application No. FR 0109628, dated Apr. 9, 2002.

French Search Report in Application No. FR 0210248, dated Apr. 11, 2003.

French Search Report in Application No. FR 9907034, dated Feb. 15, 2000.

International Search Report for International Application No. PCT/FR00/01427, mailed Sep. 6, 2000.

International Search Report for International Application No. PCT/FR02/02547, mailed Nov. 25, 2002.

International Search Report for International Application No. PCT/FR03/02435, mailed Feb. 27, 2004.

International Search Report for International Application No. PCT/FR2006/002225, mailed Apr. 4, 2007.

Office Action in U.S. Appl. No. 10/524,174, mailed May 15, 2009.

Office Action in U.S. Appl. No. 10/760,075, mailed May 26, 2009.

U.S. Appl. No. 12/083,184, filed Apr. 4, 2008, by Fortin et al.

Written Opinion for International Application No. PCT/FR2006/002225, mailed Apr. 5, 2007 (French).

Office Action dated Jul. 30, 2009, for European Patent Application No. 03778377.6 (French with English translation).

Office Action dated Nov. 4, 2009, for U.S. Appl. No. 10/524,174.

Notice of Allowance dated Jan. 25, 2010, for U.S. Appl. No. 10/760,075.

* cited by examiner

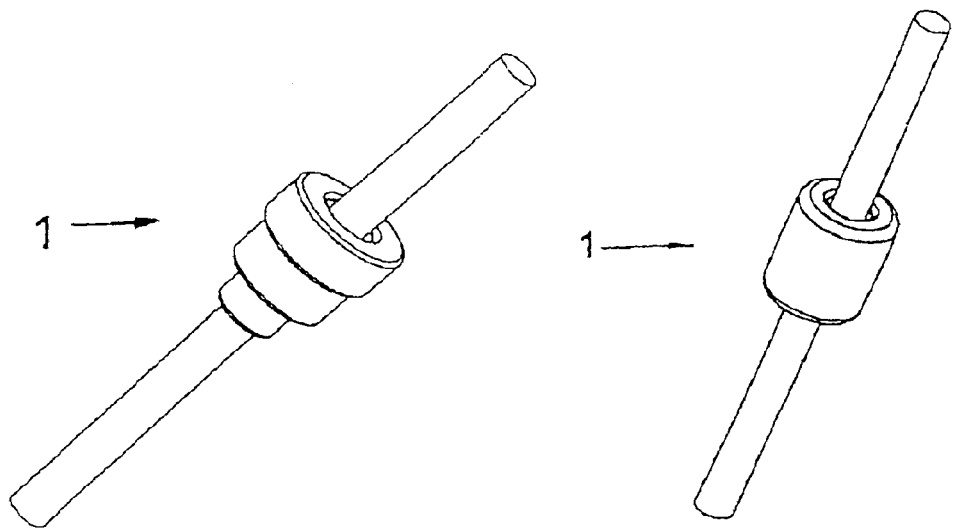
Figure 1A
Figure 1B
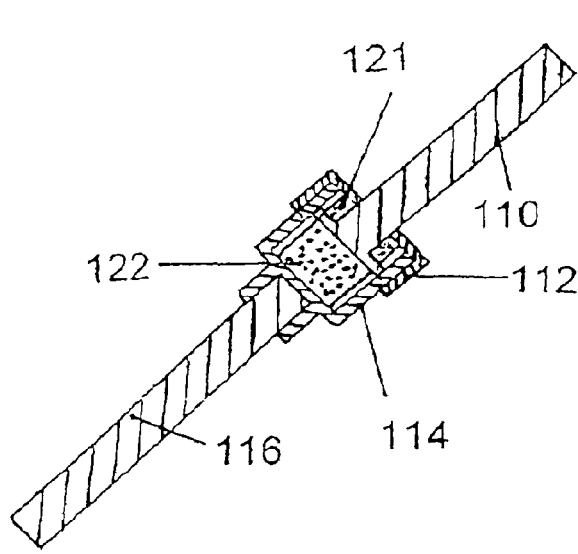
Figure 2A
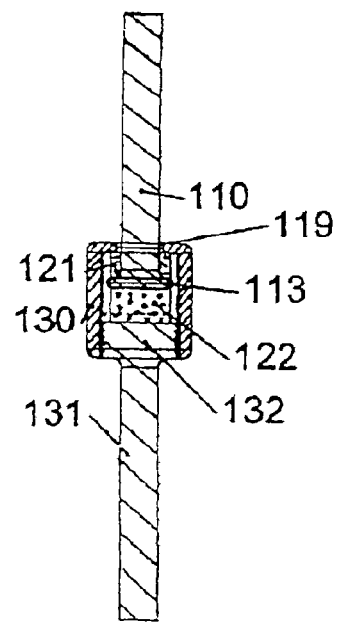
Figure 2B

FLEXIBLE VERTEBRAL LINKING DEVICE

FIELD

The invention relates to a posterior flexible vertebral linking device which works in tension, compression and flexion, and which dampens all mechanical stresses. This device has operational advantages that will be described.

BACKGROUND

Many posterior vertebral attachment units exist which rigidize a certain number of vertebrae by depriving them of any mobility, thus containing all mechanical stresses. However, the first vertebra adjacent to this rigidized block of vertebrae remains mobile and, consequently, there is an abrupt discontinuity in movement between the rigid block and this free vertebra which very often generates a very high stress in the linking elements. The result is an acceleration of the degeneration of this level (the interface between the adjacent vertebrae and the vertebrae comprising part of the rigidized block).

This problem was only partially solved by semi-rigid systems conceived to create an intermediate rigidity between the mobile vertebrae and the fixed vertebrae. These prior art systems present primarily one of two disadvantages, either they work only in tension or they work in compression with a thrust in tension.

As for those that work only in tension: this is the case of all the devices based on artificial ligaments. These systems have little elasticity and leave the care to regulate, in particular, the tension, to the skill of the operator, thus making the mechanical characteristics in the operating mode of interest (tension/compression) haphazard.

Further, those devices that work in compression with a thrust in tension are ineffective when dealing with displacements in tension.

In either case, none of the known devices entirely solves the problem which is posed, namely, damping the mechanical stresses existing in tension/compression and flexion to which a moving vertebra is subjected.

Patent Application EP 0576 379 A1 proposes a shock absorber which seems to approach most closely at least from the point of view of the general concept of this invention. This patent describes a uni-axial shock absorber working only in compression while playing the part of an abutment which opposes any displacement of the piston beyond a given value.

The invention of EP 0576379 A1 deals with the exponential limitation of the displacement, which is a completely different problem as that of the present invention.

French Patent application No. 0,012,998, describes and claims a flexible and cast solid vertebral linking device functioning in a multidirectional way. This prior art reference does not solve exactly the same problem as that of the present invention due to its different means and functions.

SUMMARY

The invention concerns a flexible intervertebral linking device that meets the needs identified above. The device (1) utilizes two sets of structures. A first structure (11) is a rigid structure (110, 112, 114, 116) preferably made of biocompatible metallic materials providing the device with good mechanical resistance by integral load transmission without deformation. A second structure (12) is a flexible or damping structure (121 and 122) made of biocompatible viscoelastic materials, permitting repeated elastic deformations, the combination of the two structures providing the device with both resistance and mechanical stress damping of forces to which it is subjected, with the purpose of compensating for any deficiency in the flexibility of certain anatomical links of the human body.

In an advantage, the surgeon can choose in a precise way the desired working method: tension/compression or flexion, or the combination of the two working methods, so as to avoid any contact between the articular facets.

BRIEF DESCRIPTION OF THE DRAWINGS

FIGS. 1A and 1B are perspective views (two alternative embodiments) of the device operating in tension, compression and flexion.

FIGS. 2A and 2B are longitudinal cross-sectional views of two alternative embodiments of the invention.

DETAILED DESCRIPTION

Figure 3:
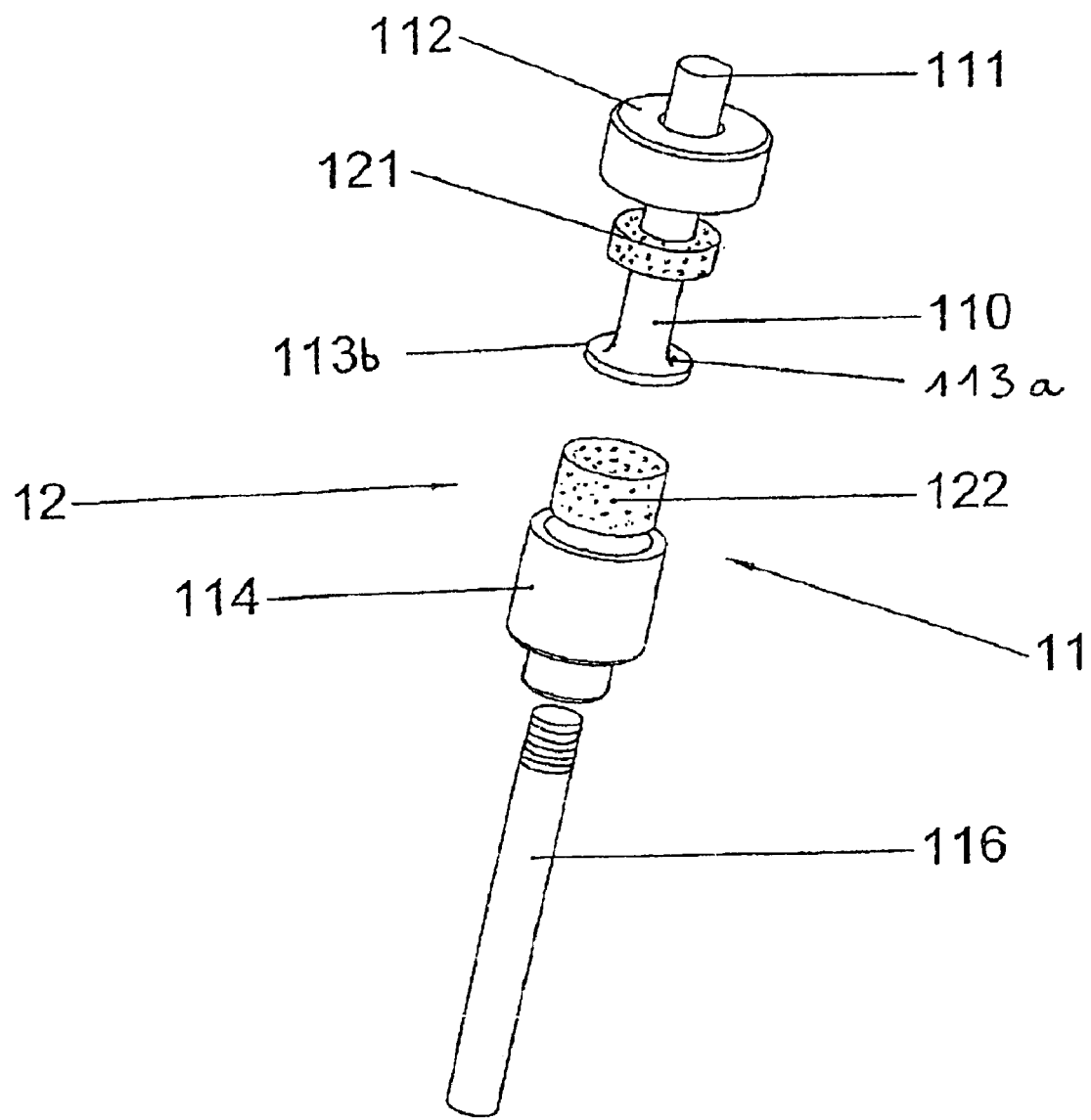
FIG. 3 is an exploded view of the invention.
Figure 4:
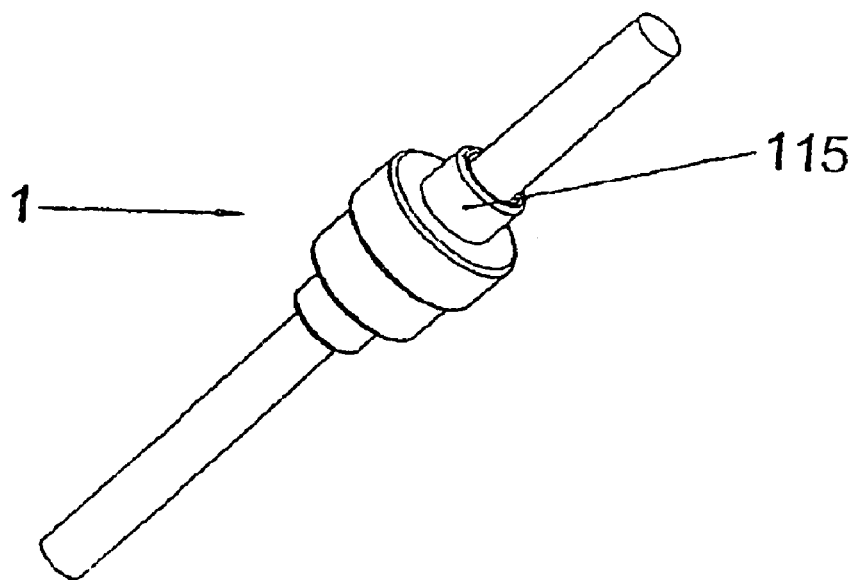
FIG. 4 is a perspective view of the invention for operation only in tension/compression.
Figure 5:
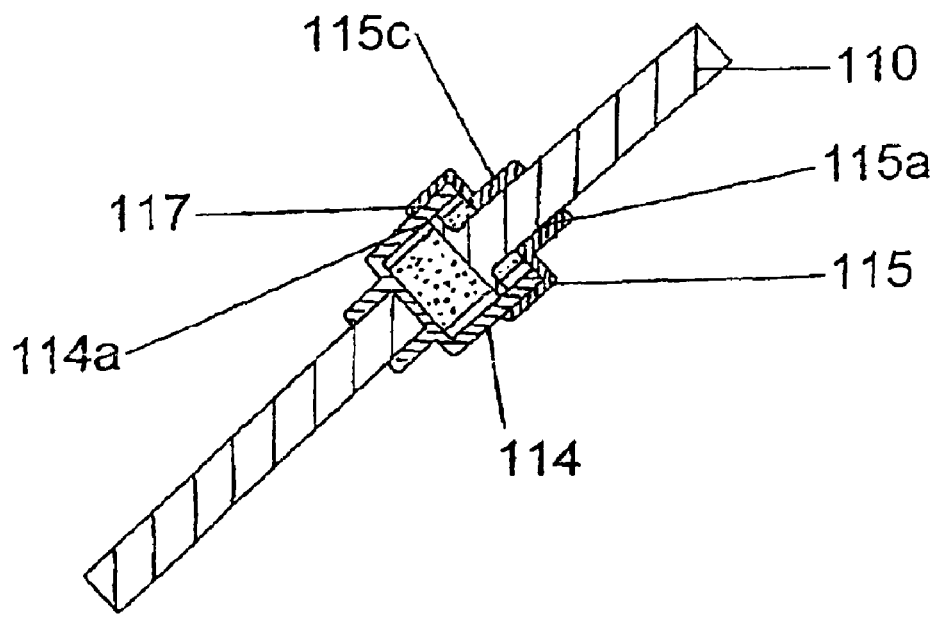
FIG. 5 is a cross-sectional view of the invention operating only in tension/compression.
Figure 6:
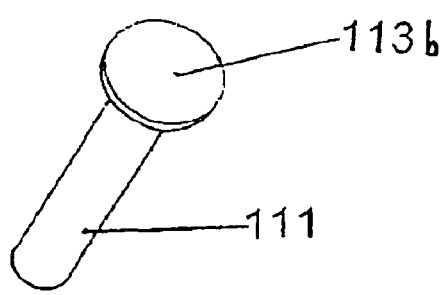
FIGS. 6 to 11 are perspective views depicting the individual parts of the invention.
Figure 7:
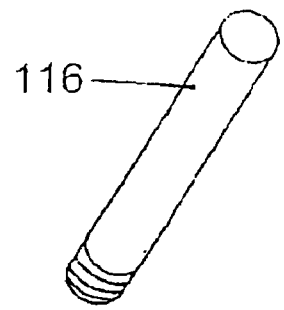
Figure 8:
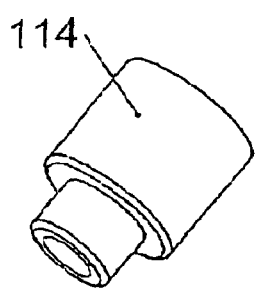
Figure 9:
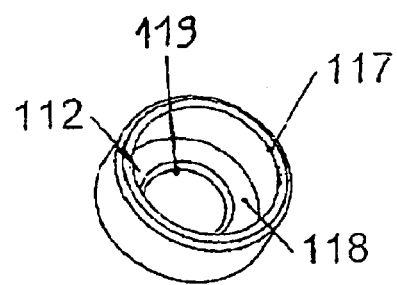
Figure 10:
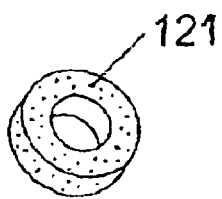
Figure 11:
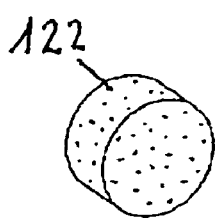
Figure 12:
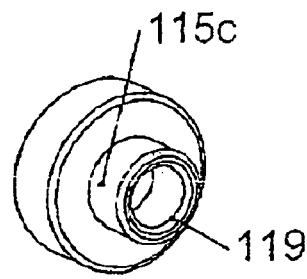
FIG. 12 is a perspective view of another component for operation in the tension/compression mode.

The device 1 utilizes two sets of structures. A first structure 11 a rigid structure manufactured out of preferably metal, biocompatible material ensuring a good mechanical resistance of the device by completely transmitting the forces.

A second structure 12 is a flexible or damping structure manufactured out of viscoelastic biocompatible materials, supporting the repeated elastic strain. It is the combination of these two structures which makes the operation of the invention possible.

The first structure 11 includes four mechanical structures 110, 112, 114, 116 which have the function of transmitting stresses to which the device 1 is subjected without deformation.

The mechanical structure 110 is made up of a mechanical rod 111, one of its ends being surmounted by a circular plate 113b connected to the rod 111 with a broad joining radius 113a, and the assembly being able to slide in the cavity of the structure 114 which encloses a visco-elastic element 121.

The mechanical structure 112 is a cap provided with a thread 117 allowing for the fixing of the structure 112 on structure 114; the structure 112 has a shoulder area 118 which encloses a viscoelastic-centering ring 121 between the plate 113b.

The mechanical structure 114 is made up of two hollow cylinders, one of which is tapped to allow the fixing of a rod 116 with a threaded end. The mechanical structure 110 and 116 will be fixed on the vertebrae to permit the functioning of the device 1.

The second structure 12 is made up of two viscoelastic components 121 and 122.

The centering ring 121 preferably allows the rod 111 to slide in its center.

The second component 122 is a disc of viscoelastic material. These two centering rings 121 and 122 can undergo compressive stresses which may not be uniformly distributed. They are formed to resist many cyclic fatigue stresses without breaking. Compressive tests have been performed which verify that the components 121 and 122 are able to undergo these tests of elastic deformation as many times as necessary.

The selected material is preferably a biocompatible polyurethane; thanks to their integration inside mechanic components 110, 112, 114, 116, the viscoelastic elements 121 and 122 are protected by the preceding mechanical structures from the aggressive environment of the human body, which avoids in particular the formation of fibers around these components which could deteriorate the viscoelastic properties of the material and consequently disturb the correct operation of device 1.

This device 1 makes possible the damping of the stresses in tension/compression and flexion which it undergoes by the intermediary of rods 110 and 116. This function is assured owing to the fact that component 112 has a sufficiently broad opening 119 to allow a clearance of rod 111 and that there is a functional allowance between plate 113 and the hollow body of component 114; the shoulder area 118 serves as a stop and maintains in its housing the viscoelastic element 121 thus constrained.

If one wishes to work in a uni-axial mode of tension/compression, component 112 is replaced by another component 115 equipped with threads 117, which includes a cap 115c, whose opening 119 is of a diameter which corresponds to the diameter of the rod 110 and which is elongated with a rod guide 115a.

This device 1 is thus able to react dynamically to the applied stresses. Note that it is essential that structure 114 comprises a bore 114a to allow for low friction guidance of rod 110 in the aforementioned component 114.

The adjustment of the diameter of the viscoelastic centering rings 121 and 122 must be selected with precision to enable them to be crushed freely until a stress threshold is reached, this threshold corresponding to a point of contact of the bore 114a of component 114.

An alternative to the structure 11 includes metal structures having the same functions as the structures 110, 112, 114, 116, but the assembly of these three parts (110,130, 131) having a lower threshold than that of the structures previously described (see FIG. 2).

The rod 131 is fixed at its cap 130 by the intermediary of a thread located on shoulder 132 of the rod.

In this alternative embodiment, the possibilities of displacement of rod 110 subjected to the stresses in flexion are enabled by play 119 located between cap 130 and rod 110.

For a uni-axial operation of device 1, it is preferable to use components 110,112, 114, 116 which provide a better guidance of rod 110. If small overall dimensions are needed, components 110, 130, 131 may be preferably used.

Figure 13:
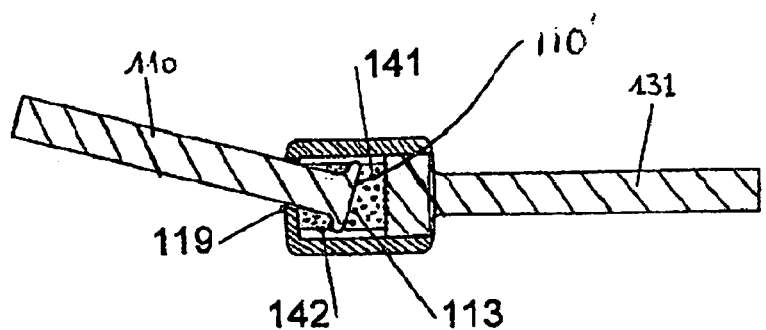
FIG. 13 is a side, cross-sectional view of an alternative of the device working along two axes.

Device 1 is able to function with rods 110 and 131 moving on convergent axes (FIG. 13) with a small angle of displacement and according to given clearances.

The structure 12 is therefore comprised of two visco-elastic components 141 and 142. Note that the rod 110 has a flange 110' on its end. The component 141 is a cylinder of visco-elastic biocompatible material whose face in contact with the flange 110' is inclined. The component 142 is a centering ring whose face in contact with the back of the flange 110' is inclined.

The structure 11 (rigid means) is identical to the previous one that is described above, the orifice 119 being however eccentric depending on the chosen angle. The shape of orifice 119 is defined depending on the clearances allowed with the rod 110.

Figure 14:
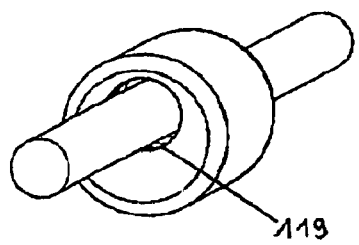
FIGS. 14 to 17 are perspective views of four forms of the mobile end of other embodiments of the invention.

The rod 110 is thus able, thanks to these new technical characteristics, to function in tension/compression with a given angle with respect to the rod 116 or the rod 131 in the case in which the 119 orifice is eccentric and adjusted to the rod 116 or 131 (see FIG. 14).

Figure 15:
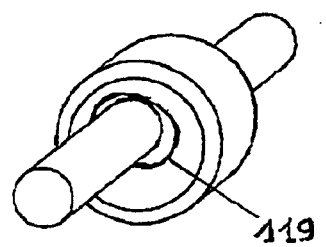

The rod 110, forming an angle with respect to the rod 116 or 131 (the case in which the 119 orifice is oblong and eccentric), can in this case function equally well in tension/compression as in lateral flexion. (see FIG. 15).

Figure 16:
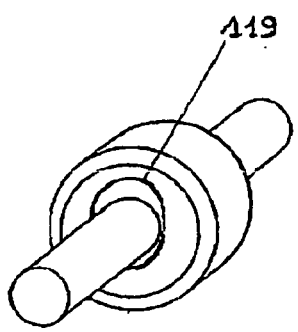

The rod 110 can function in tension/compression and in flexion following a preferred axis which can be, for instance, in the sagital plane of the spinal column, and this one on the one side and one the other side of a given position of the rod 110 which, at rest, forms an angle with the rod 116 or the rod 131, this also being the case where the component 119 is oblong or eccentric, (FIG. 16).

Figure 17:
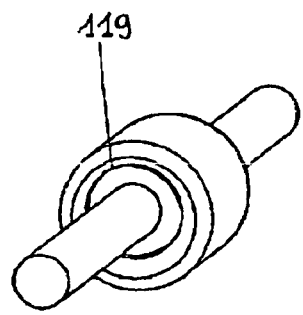
Figure 18:
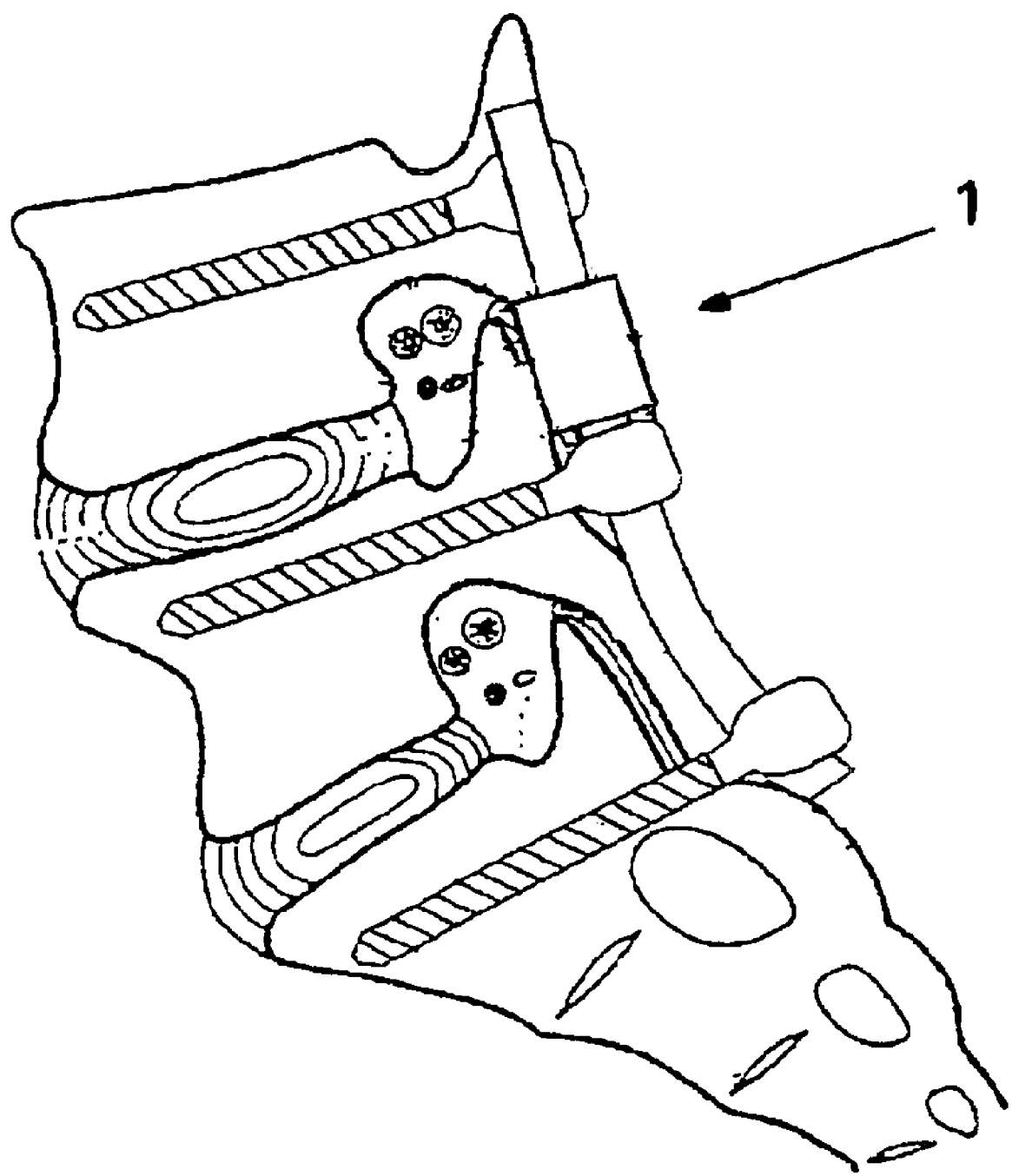
FIG. 18 is a side, cutaway view of the invention in place in a patient.

Finally, the rod 110 can function in tension/compression and in flexion in all directions, forming an angle, as against the rod 116 or 131 in case the orifice 119 is eccentric or larger than the diameter of the rod 110 (see FIG. 17).

Multiple varitions and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

The invention claimed is:

1. A flexible vertebral linking device, comprising:
   a cylindrical body portion having a first end and a second end;
   a first rod portion extending from the first end in a first direction from the cylindrical body portion;
   a second rod portion having a first elongated body and an enlarged end portion, wherein the enlarged end portion is positioned within the cylindrical body portion and configured to pivot within the cylindrical body portion to adjust the alignment of the second rod portion with respect to a longitudinal axis of the cylindrical body portion, and wherein the first elongated body extends in a second direction opposite the first direction and passes through an opening in the cylindrical body portion second end, the opening in the cylindrical body portion second end having a width that is less than a width of the enlarged end portion but is greater than a width of the first elongated body;
   a first dampening member positioned between the enlarged end portion and the cylindrical body portion first end such that the first dampening member does not encircle any portion of the second rod portion; and
   a second dampening member positioned between the enlarged end portion and the cylindrical body portion second end.

2. The flexible vertebral linking device of claim 1, wherein the cylindrical body portion second end comprises a cap.

3. The flexible vertebral linking device of claim 2, wherein the cap includes a threaded inner region.

4. The flexible vertebral linking device of claim 1, wherein the first rod portion includes a threaded end configured to engage a threaded portion of the cylindrical body portion.

5. The flexible vertebral linking device of claim 1, wherein the second dampening member includes a ring shape with an opening configured to receive the first elongated body of the second rod portion.

6. The flexible vertebral linking device of claim 1, wherein the opening in the cylindrical body portion second end is circular.

7. The flexible vertebral linking device of claim 1, wherein the opening in the cylindrical body portion second end is eccentrically located on the cylindrical body portion second end.

8. The flexible vertebral linking device of claim 1, wherein the opening in the cylindrical body portion second end includes an oblong shape having at least one dimension that is greater than the width of the first elongated body.

9. A method of joining vertebral implants, comprising:
   providing a cylindrical body portion having a first end and a second end;
   connecting a first rod portion extending from the first end in a first direction;
   positioning a first dampening member within the cylindrical body portion;
   positioning a part of a second rod portion having a first elongated body and an enlarged end portion within the cylindrical body portion such that the first dampening member is located between the enlarged end portion and the cylindrical body first end and the first dampening member does not encircle any portion of the second rod portion;
   positioning a second dampening member between the enlarged end and the cylindrical body portion second end; and
   placing a cap having an opening that includes a width that is less than a width of the enlarged end portion of the second rod portion and is greater than a width of the first elongated body over the second rod elongated body such that the elongated body passes through the opening and the enlarged end portion is secured within the cylindrical body portion,
   wherein the enlarged end portion is configured to pivot within the cylindrical body portion to adjust the alignment of the second rod portion with respect to a longitudinal axis of the cylindrical body portion.

10. The method of claim 9, wherein the cap includes a threaded inner region.

11. The method claim 9, wherein the first rod portion includes a threaded end configured to engage a threaded portion of the cylindrical body portion.

12. The method of claim 9, wherein the second dampening member includes a ring shape with an opening configured to receive the first elongated body of the second rod portion.

13. The method of claim 9, wherein the opening in the cap is circular.

14. The method of claim 9, wherein the opening in the cap is eccentrically located on the cylindrical body portion second end.

15. The method of claim 9, wherein the opening in the cap includes an oblong shape.

* * * * *

UNITED STATES PATENT AND TRADEMARK OFFICE
CERTIFICATE OF CORRECTION

| | |
|---|---|
| PATENT NO. | : 7,776,071 B2 |
| APPLICATION NO. | : 10/505469 |
| DATED | : August 17, 2010 |
| INVENTOR(S) | : Frederic Fortin and Johann Robin |

It is certified that error appears in the above-identified patent and that said Letters Patent is hereby corrected as shown below:

On the Title Page,

Insert Item -- (30) Foreign Application Priority Data

Jul. 18, 2001 (FR) .................... 01/09628 --

Signed and Sealed this
Fifteenth Day of February, 2011

David J. Kappos
*Director of the United States Patent and Trademark Office*